US005466448A

United States Patent [19]
Smart, Jr. et al.

[11] Patent Number: 5,466,448
[45] Date of Patent: * Nov. 14, 1995

[54] BIOLOGICAL CONTROL OF ORTHOPTERA PEST INSECTS

[75] Inventors: Grover C. Smart, Jr.; Khuong B. Nguyen, both of Gainesville, Fla.

[73] Assignee: University of Florida Research Foundation, Inc., Gainesville, Fla.

[*] Notice: The portion of the term of this patent subsequent to Nov. 24, 2009, has been disclaimed.

[21] Appl. No.: 235,137

[22] Filed: Apr. 28, 1994

Related U.S. Application Data

[63] Continuation of Ser. No. 3,574, Jan. 13, 1993, abandoned, which is a continuation-in-part of Ser. No. 957,771, Oct. 7, 1992, abandoned, which is a division of Ser. No. 453,806, Dec. 20, 1989, Pat. No. 5,165,930, which is a continuation-in-part of Ser. No. 406,825, Sep. 12, 1989, abandoned, which is a continuation of Ser. No. 895,385, Aug. 11, 1986, abandoned.

[51] Int. Cl.[6] ........................... A61K 35/56; A01N 63/00
[52] U.S. Cl. .................. 424/93.1; 424/405; 424/93.7; 800/2; 119/6.7
[58] Field of Search ................... 424/405, 93.1, 424/406, 1, 93.7; 800/2, DIG. 4, DIG. 5, DIG. 3; 119/6.7

[56] References Cited

U.S. PATENT DOCUMENTS

| 4,608,367 | 8/1986 | Endo et al. | 514/89 |
| 5,165,930 | 11/1992 | Smart et al. | 424/93.1 |

OTHER PUBLICATIONS

Nguyen et al. 1989 J. Nematol. 21, 576.
Nematology Circular No. 136. (Fla. Dept. Agric. Consumer, Serv. Div. of Plant Industry), Publ. Dec. 1986.
Smart et al. 1984. in: First Intl. Congress of Nematology, Guelph, Ontario, Canada. 5–10 Aug. p. 95, abstract 253.
Shapiro et al. 1985. J. Econ. Entomol. 78, 342–345.
Gaugler, R. 1981. J. Nematol. 13, 241–249.

Primary Examiner—Christopher S. F. Low
Attorney, Agent, or Firm—Kerkam, Stowell, Kondracki & Clarke; Dennis P. Clarke

[57] ABSTRACT

A method, composition and product for biologically controlling pest insects exclusive of mole crickets in the order Orthoptera based on the insecticidal nematode *Steinernema scapterisci* having ATCC No. 75197.

2 Claims, No Drawings

BIOLOGICAL CONTROL OF ORTHOPTERA PEST INSECTS

RELATED APPLICATIONS

This is a continuation of application Ser. No. 08/003,574 filed Jan. 13, 1993 now abandoned, which is a continuation-in-part of Ser. No. 07/957,771 filed Oct. 7, 1992 now abandoned which is a divisional of Ser. No. 07/453,806 filed Dec. 20, 1989 now U.S. Pat. No. 5,165,930 which is a continuation-in-part of Ser. No. 07/406,825 filed Sep. 12, 1989 now abandoned which is a continuation of Ser. No. 06/895,385 filed Aug. 11, 1986 now abandoned. This application is a continuation-in-part of application Ser. No. 07/959,771 filed Oct. 7, 1992, which is a division of application Ser. No. 07/453,806 filed Dec. 20, 1989 (now U.S. Pat. No. 5,165,930 issued Nov. 24, 1992), which is a continuation-in-part of application Ser. No. 07/406,825 filed Dec. 12, 1989 (now abandoned), which was a continuation of Ser. No. 06/895,385 filed Aug. 11, 1986 (now abandoned).

BACKGROUND OF THE INVENTION

Field of the Invention

The present invention relates to the biological control of insects in the order Orthoptera.

Discussion of the Prior Art

Mole crickets (*Scapteriscus acletus, S. vicinus* and *S. abbreviatus*) were introduced accidentally into Florida from South America [Walker et al, Ann. Entomol. Soc. Am., Vol. 74, pages 158–163 (1981)]. It has been reported that there is no economical method of controlling mole crickets in the United States [Nickle et al, Ann. Entomol. Soc. Am., Vol. 77, pages 450–465 (1984)]. Chemical control with insecticides has been attempted [Ismailov et al, Zashch. Rast. (Moscow), Vol. 160, page 32 (1981); Loutfy et al, Agric. Res. Rev., Vol. 55, No. 1, pages 193–195 (1977); Noguchi et al, Shikoku Shokubutsu Boeki Kenkyci, Vol. 11, pages 23–28 (1976); Bastos et al, Fitossamidade, Vol. 2, No. 2, pages 57–58 (1977); Short, Down Earth, Vol. 29, No. 1, pages 26–29 (1973); Chari et al, Pesticides, Vol. 7, No. 3, pages 16–17 (1973); Vinnichenko, Tr. Kishinet, Selskehoz. Inst., Vol. 88, pages 90–92 (1972); Vinnichenko, ibid, vol. 66, pages 182–191 (1971); van Middelem et al, J. Econ. Entomol., Vol. 65, No. 2, pages 495–497 (1972); Beck et al, ibid, Vol. 60, No. 6, pages 1517–1519 (1967)], but has not proved practical because of the cost of treating an area and the need for re-treatment due to re-invasion of mole crickets from untreated areas into the treated areas.

It is known that the infective stages of certain nematodes are insecticidal to certain insects. It has been suggested to utilize various insect-parasitic nematodes for biologically controlling various insects. U.S. Pat. No. 4,178,366 discloses an insecticidal composition containing infective larvae of the nematode *Neoaplectana carpocapsae* [Agriotos strain for biologically controlling a wide variety of insects such as the codling moth (*Cydia pomonella*), the southern ironbark beetle (*Dendroctonus frontalis*), larch sawfly larvae (*Pristophora erichsonii*), Colorado potato beetle (*Leptinotarsa decemlineata*), cabbage white butterfly (*Pieris rapae*), cutworms (*Persectania ewingi* and *Euromessoria sp.*), eucalyptus sawflies (*Perga afinis* and Pterygophorus), the cup moth (*Doratifera sp.*), the autumn gum moth (*Mnesampela privata*) and the chrysomelids (*Chrysophtharta nobilitata, C. decolorata, C. aureous, Paropsisterna nucea, Paropsis lutea* and *P. charybdis*)].

U.S. Pat. No. 4,615,883 describes an insecticidal composition containing nematodes having insecticidal activity against a wide variety of insects.

Serczynska [Bull. Acad. Pol. Sci. Ser. Sci. Biol., Vol. 26, No. 2, pages 103–106 (1978)] reports that a composition of tribunil and *Neoaplectana carpocapsae* (Weiser) was effective against the Colorado beetle.

Burman [Nematologica, Vol. 28, No. 1, pages 62–70 (1982)] reports on the insecticidal toxin produced by the nematode *Neoaplectana carpocapsae*.

Fowler et al [Rev. Brasil. Biol., Vol. 43, pages 789–795 (Nov. 1988); Naturwirrenschaften, Vol. 76, pages 26–27 (1989); and Intl. Rice Research Newsletter, Vol. 13, pages 34–35 (1988)] report on research directed toward the control of, among others, mole crickets utilizing the nematodes *Steinernema feltiae*.

Biosys, Inc., currently markets a product called "BioSafe," and Biologic, Willow Hill, Penna., markets a product called "Scanmask," both containing *Neoaplectana carpocapsae* (=*Steinernema feltiae*) which are said to be useful for controlling mole crickets. A disadvantage associated with these strains, however, is that they reproduce little or none in mole crickets and, therefore, recycle little or not at all in nature.

The utilization of most strains of insect-parasitic nematodes for biologically controlling insects also suffers from several other disadvantages.

Thus, most strains of the nematode *Neoaplectana carpocapsae* demonstrate little host specificity and will parasitize, infect with toxin and kill a wide variety of insects. Where it is desired to kill only a certain or a few species of insects, most strains of nematodes generally represent a poor choice for biological control since they may infect and kill beneficial insects as well.

It is an object of the present invention to provide an insecticidal composition and a method of controlling pest insects in the order Orthoptera, e.g., cockroaches, grasshoppers, locusts, mole crickets, house crickets, field crickets, Mormon crickets, etc., utilizing a heretofore unknown nematode.

SUMMARY OF THE INVENTION

The foregoing and other objects are realized by the present invention which provides a method of biologically controlling pest insects in the order Orthoptera comprising contacting so as to infect the insects with an insecticidal amount of infective third stage of *Steinernema scapterisci* nematodes having ATCC No. 75197.

Another embodiment of the invention comprises a composition for the biological control of pest insects in the order Orthoptera comprising an insecticidally effective amount of infective third stage of *Steinernema scapterisci* nematodes having ATCC No. 75197 and an inert carrier therefor.

An additional embodiment of the invention comprises the infective third stage of *Steinernema scapterisci* nematodes having ATCC No. 75197 produced by passage of a first infective third stage of the nematodes through insects in the order Orthoptera to produce a second infective third stage of the nematodes having a greater degree of insecticidal activity than the first infective third stage.

A final embodiment of the invention comprises the infective third stage of *Steinernema scapterisci* nematodes having ATCC No. 75197 produced by serial passage of the first infective third stage of the nematodes through insects in the order Orthoptera to produce the infective third stage of the nematodes having a greater degree of insecticidal activity than the first infective third stage.

DETAILED DESCRIPTION OF THE INVENTION

The research which led to the description of the invention in parent application Ser. No. 06/895,385 erroneously characterized the mole cricket infective nematode as *Steinernema carpocapsae* (=*Neoaplectana carpocapsae*= *Steinernema feltiae*). Further research on the biology and morphology of the nematode has revealed that the nematode is not *S. carpocapsae*, but rather a heretofore unknown species designated *Steinernema scapterisci*. The nematode, a natural enemy of mole crickets, was found in Brazil and Uruguay.

The genus Steinernema was erected by Travassos in 1927 [Travassos, Sobre o Genera Oxysomatium, Boletim Biologico, Vol. 5, pages 20–21 (1927)] to contain the species *Aplectana kraussei* which Steiner [Steiner, n. sp., eine in der Blattwespe Lyda sp. Parasitierende Nematodenform, nebst Bemerkugen uber das Seitenorgan der parasitichen Nematoden. Centralblatt fur Bakterien und Parasitenkunde, Vol. 59, pages 14–18 (1923)] had described in 1923 from the sawfly (*Cephaleia abietis*). Travassos created the new genus due to differences in morphology and because this species was a parasite of insects, while all other species in the genus Aplectana were intestinal parasites of Amphibiae.

Steiner [Journal of the Washington Academy of Science, Vol. 19, pages 436–440 (1929)] established the genus Neoaplectana in 1929 to contain the type species *N. glaseri* which he described from the Japanese beetle (*Popillia japonica*). Later, other species such as *N. feltiae* [Filipjev, 1934] from the cutworm, *N. bibionis* [Bovien, 1937] from bibionid larvae, and *N. carpocapsae* [weiser, 1955] from the codling moth were added to the genus. Poinar [Nematodes for biological control of insects, Boca Raton, Fla., CRC Press (1979)] revised the genus Neoaplectana adding more details to the description of some species and constructing a key to identify the species contained in the genus. According to Filipjev [Miscellanea Nematologica, I. Eine neue Art der Gattung Neoaplectana nebst Bemerkugen uber die systematische Stellung der letzteren. Magazin fur Parasitologie des Zoologischen Instituts der Akademie der Wissenschaften der UdSSR, Vol. 4, pages 229–240 (1934)] and other authors [Bedding, Nematode parasites of Hymenoptera, pages 755–795 in Nickle, ed., Plant and insect parasitic nematodes, New York, Marcel Dekker (1984); Mrazek et al, Head and cuticular structures of some species in the family Steinernematidae (Nematoda), Nematologica, Vol. 27, pages 443–448 (1981); Wouts, Parasites of lepidopterans, pages 655–696 in Nickle, ed., Plant and insect parasitic nematodes, New York, Marcel Dekker (1984)]. Neoaplectana closely resembles Steinernema. Wouts et al [Neoaplectana, Steiner, 1929, a junior synonym of Steinernema; Travassos, 1927 (Nematoda: Rhabditida), Systematic Parasitology, Vol. 4, pages 147–154] demonstrated to their satisfaction that the two genera are identical and thus considered Neoaplectana to be a junior synonym of Steinernema. We concur with these authors and use the generic name Steinernema for the new species described herein, as well as for other species of this group [Nguyen et al, Journal of Nematology, Vol. 22, pages 187–199 (1990) and Nguyen et al, Journal of Nematology, Vol. 24, No. 4, pages 478–481 (in press, 1992)].

Third stage infective nematodes of the genus Steinernema carry with them, in the anterior part of the intestine, a pellet of live bacteria. *S. scapterisci* carries a bacterium which is probably a new species in the genus Xenorhabdus. When the third stage (the third stage is the only infective stage, i.e., capable of entering an insect) enters the host, usually through its mouth, the nematode goes to the intestine of the insect, penetrates through the intestinal wall and enters the body cavity which is filled with body fluid (hemolymph). In the body cavity, the third stage nematode changes to a feeding third stage juvenile. As it does so, it releases the pellet of bacteria into the body fluid. The bacteria multiply rapidly and the nematode feeds on the bacteria and almost certainly engulfs the body fluid also. After a period of feeding, the third stage juvenile molts (sheds its skin) to become the fourth stage and subsequently molts one more time to become an adult. Males and females mate and the females lay eggs. The eggs hatch and the juveniles continue development through the adult stage. Again, mating takes place and the females lay eggs. These eggs hatch and the juveniles develop to the third stage. These third stage juveniles collapse the anterior portion of the intestine around a pellet of living bacteria and leave the cadaver in search of a new host insect. The length of the life cycle is somewhat temperature-related, but takes place in about 4–10 days.

Since males and females are necessary for reproduction, both male and female juveniles must enter an insect for reproduction to occur, but a single nematode can cause death of the insect because the bacteria it releases causes septicemia. Before the work of Burman, supra, it was thought that the bacteria alone caused death of the insect, but it appears that the nematode may also play a role.

Although *S. scapterisci* is useful for the control of any pest insect species in the order Orthoptera, the present invention is predicated on the discovery that *S. scapterisci* is particularly host-specific to mole crickets (i.e., *Scapteriscus spp.*), specifically *S. acletus, S. vicinus, S. abbreviatus* (imported mole crickets), *Neocurtilla hexadactyla* (native mole cricket) and *Acheta domestica* (house cricket) as an insect parasite and is particularly insecticidally specific to mole crickets and house crickets, as opposed to other insects not in the order Orthoptera.

Unexpectedly, *S. scapterisci* is relatively non-parasitic and non-insecticidal to most other insects, e.g., granulate cut worm (*Agriotis subterranea*), wax moth larvae (*Galleria mellonella*), honeybees (*Apis mellifera*), etc.

*S. scapterisci* nematodes collected in Uruguay were inoculated into mole crickets which were hand-carried to Florida. In Florida, populations of the nematode were increased in the mole crickets (*Scapteriscus vicinus* and *S. acletus*) and later in the house cricket (*Acheta domestica*). The population selected originally killed only 38% of the mole crickets; however, by serial passage through mole crickets, the kill rate was increased to 100%. These nematodes (or their progeny) were used for all studies herein.

Nematodes used for morphological studies were obtained as described below. Mole crickets were infected with the third stage (infective stage) juvenile of *S. scapterisci*. After the mole crickets died, first generation adults were collected in 2–3 days, second generation adults in 5–7 days, and third stage juveniles in 7–15 days. The nematodes were killed in warm water (40° C.) and mounted in water on glass slides with coverglass supports. In addition, many live nematodes or nematodes killed and stained with acid fuchsin were observed to confirm the presence and/or nature of some anatomic structure.

Nematodes prepared for scanning electron microscopy (SEM) were placed live in lactophenol at 43° C. for 30 minutes, transferred to a desiccator for two days, removed, rinsed with water and then prepared by the method of Stone et al [Nematologica, Vol. 17, A simple method of preparing nematodes for scanning electron microscopy, pages 490–491 (1971)]. Specimens were examined in a Hitachi S450 SEM.

To prepare spicules and gubernacula for SEM, male nematodes of the first generation were placed in a petri dish containing water, killed by low heat and stored at room temperature. After 2–3 days when the bodies had softened due to decay, they were transferred to clean water and, with two small needles, the rear portion of each nematode was torn open, the spicules and gubernaculum were dissected out and washed free of debris by sloshing them about in water. Then the spicules and gubernaculum were picked up with a needle and placed close to a hair used as a marker on a previously prepared SEM stub.

Cross hybridization studies were conducted using two different techniques. In one technique, a drop of blood (hemolymph) from a mole cricket was placed in a 35×10 mm sterile petri dish and one third-stage juvenile of *S. scapterisci* and one of *S. carpocapsae* strain Breton was added. The dish was placed in a plastic bag containing a paper towel saturated with water. The plastic bag was closed, tied and stored in the dark. The treatment was replicated 25 times.

In the second technique, two drops of blood were prepared as above and ten third-stage juveniles of *S. scapterisci* were placed in one drop and ten third-stage juveniles of *S. carpocapsae* strain Breton were placed in the other drop. Then they were handled as above. The treatment was replicated ten times for each nematode. The nematodes were observed daily and, when the sexes could be distinguished but before they became adults, all males in the dishes of *S. scapterisci* were removed and placed in a separate drop of blood. Similarly, the males of *S. carpocapsae* strain Breton were removed and placed in a separate drop of blood. Then the males of *S. scapterisci* were transferred to the drop of blood containing females of *S. carpocapsae* strain Breton, and males of *S. carpocapsae* strain Breton were transferred to the drop of blood containing females of *S. scapterisci*. The nematodes were observed frequently to see if they mated and produced offspring. Nematodes of each species were retained in drops of blood in two dishes as controls.

Four species of insects in the order Lepidoptera [fall army worm (*Spodoptera frugiperda*), velvet bean caterpillar (*Anticarsia gemmatalis*), granulate cut worm (*Feltia subterranea*) and greater wax moth larvae (*Galleria mellonella*)] were used to compare the rate of kill by *S. scapterisci* to that of some other species and strains of Steinernema.

Two pieces of Whatman No. 2 filter paper were placed in a 100×15 mm petri dish and 8,000 third stage juvenile nematodes in 2 ml water, and ten insects were added. Controls were prepared similarly, but without nematodes. Treatments were replicated four times. After two days, the number of dead insects was determined.

Measurements for first and second generation females are presented in Table 1; those for first and second generation males in Table 2; and those for third stage juveniles in Table 3.

Holotype (male, first generation):
 Total length=1554 μm
 Greatest width=131 μm
 Length of stoma=3.9 μm
 Width of stoma=6 μm
 Head to excretory pore=77 μm
 Head to nerve ring=130 μm
 Head to end of esophagus=189 μm
 Testes from reflexion to terminus=416 μm
 Body width at anus=37.5 μm
 Tail length=28 μm
 Spicule length=89 μm
 Spicule width=13.5 μm
 Gubernaculum length=65 μm
 Gubernaculum width=7.8 μm
 Mucron length=4.5 μm
Allotype (female, first generation:
 Total length=4875 μm
 Greatest width=200 μm
 Length of stoma=7.8 μm
 Width of stoma=11 μm
 Head to excretory pore=78 μm
 Head to nerve ring=181 μm
 Head to end of esophagus=265 μm
 Body width at anus=73 μm
 V=50%

Description—Females, First Generation

Body cuticle smooth, lateral fields and phasmids not observed. Head rounded, continuous with body, and bearing both labial and cephalic papillae. Six lips, united at base, each terminating in a labial papilla. The six labial papillae are not evenly distributed when viewed en face. While the two subventral and two subdorsal papillae are located as expected, the two lateral papillae are located ventrolaterally making the ventral and lateral papillae closer together than are the lateral and dorsal papillae. Apex of each papilla usually covered with a thin layer of whitish (electron lucent) material. Four cephalic papillae present, but not always distinct. Amphids not observed. Stoma very shallow, circular anteriorly, then becomes subtriangular.

Cheilorhabdions prominent, unusually thickened, appearing as a circular or hexagonal ring en face. Prorhabdions, just posterior to cheilorhabdions, also quite distinct. Posterior to prorhabdions, no other sclerotized structures observed. Esophagus typical of the Steinernematide, i.e., muscular throughout with a procorpus, slightly swollen, nonvalvate metacorpus, isthmus and basal bulb with a small, but quite visible, valve. Nerve ring located in isthmus region of esophagus. Esophago-intestinal valve long and prominent. Excretory pore located anteriorly to mid-metacorpus. Excretory duct unusually prominent forming a small loop midway between excretory pore and base of esophagus, then turning to right side of esophagus, or sometimes extending to anterior part of intestine, then returning on ventral side of intestine at its junction with the esophagus; here appears an elliptically-shaped structure seemingly with a hole at the center. A uninucleate gland is located posteriorly to this structure, but a junction of the excretory duct with the gland has not been observed. This elliptically-shaped structure has been seen in almost every first generation female and is visible even with a dissecting microscope. Gonads didelphic, opposed; ovaries reflexed. Vulva appears as a transverse slit with a prominent double-flapped epiptygma. Vagina sclerotized, its length about ⅓ body width at vulva, and leading to paired uteri. Body width anterior to vulva always greater than that posterior to vulva. Tail somewhat variable in shape, but usually has a post-anal swelling ventrally and a mucron at its terminus; length of tail less than width of body at anus. Pygmy form of first generation females referred to for other species by Bovien [Some types of association between nematodes and insects. Videnskabelige Meddelelser Fra Dansk Naturhistorisk Forening, Vol. 101, pages 1–114 (1937)] not observed.

Female, Second Generation

Second generation female similar morphologically to that of first generation with the following exceptions: about one-half as long and two-thirds as wide, valve in basal bulb of esophagus more prominent, elliptically-shaped structure less prominent; tail, which tapers to a point bearing a mucron, longer than body width at anus.

Male, First Generation

First generation male much smaller than first generation female, but anatomically the two are similar anteriorly. Body usually plump, nerve ring located in isthmus region of esophagus, but exact position variable. Excretory duct not forming elliptically-shaped structure present in females. Posterior part of body curved ventrally. Body assumes a spiral shape when killed by minimal heat. Gonad one, testis reflexed. Spicules dark brown in color, paired, uniformly curved with head large and somewhat angular. Angle formed by shaft and blade of spicules averages 110° (range 100°–120°). Shaft of spicules long when compared to those of other species of the genus, and appears to be encased in a sheath; blade tapers smoothly to end with posterior portion thinner than that for other species of Steinernema. In cross-section, blade of spicule contains two lumina, but only one aperture was seen on ventral side close to tip. Aperture smaller than that in spicule of other species in the genus. Each spicule has two internal ribs with variable termination point proximally. Ribs appear to be strengthening structures of upper and lower walls between the two lumina of the blade. Gubernaculum boat-shaped, with anterior part thin, long and ventrally-curved and posterior end bifurcate. Compared to S. carpocapsae strain Breton, the anterior part of the gubernaculum of S. scapterisci is much longer. Spicules glide along gubernaculum in two grooves separated by a ridge. Cloaca on a raised area bearing an anterior flap, seen easily when the spicules are projected or retracted. Ten pairs and one single genital papillae observed with pairs 1 and 6 difficult to see. The single papilla is located ventrally and between pairs 4 and 5; pairs 1–9 are located ventrolaterally and pair 10 subdorsally. Tail bears a mucron, posterior region always curved ventrally.

Male, Second Generation

Second generation male similar morphologically to that of the first generation, except that it is about two-thirds as long and one-half as wide and the spicules have an elongated head.

Juveniles, Third Stage

Measurements are given in Table 3. The third stage juvenile is the infective stage, and when newly formed, it is always enclosed in the cuticle of the second-stage juvenile as a sheath. However, the sheath is lost rather easily, even in storage, and thus may not always be present. Body thin, lip region not offset, oral aperture not observed. Esophagus degenerate and thus not seen clearly, but its basal bulb is elongate and has a valve. Lateral field with 6 incisures. Tail tapers gradually dorsally, but abruptly ventrally.

Type designations

Holotype (male of the first generation), slide number T-432t, USDA Nematode Collection, Beltsville, Md. Paratypes are distributed as follows: 10 males and 10 females of the first generation and several third stage juveniles in lactophenol in a vial, vial number T-318p USDA Nematode Collection, Beltsville, Maryland; 1 male and 1 female and 11 third stage juveniles, UCNC slide numbers 2406 and 2407, respectively, California Collection of Nematodes, University of California, Davis, Calif.; 1 male and 1 female, and 10 third stage juveniles, slide numbers T 99 N89-694, Florida Collection of Nematodes, Florida Department of Agricultural and Consumer Services, Gainesville, Fla. The nematode population is being maintained at the Nematology Lab, Entomology and Nematology Department, University of Florida, Gainesville, Fla.

In cross hybridization experiments, males and females never mated and thus no offspring were produced. In the controls, males and females mated and offspring were present after ten days.

Except for S. scapterisci, all species of Steinernema tested, including all strains of S. carpocapsae, killed from 20–100% of the test insects; S. scapterisci killed no more than 10% (Table 4). The difference in the percentage of wax moth larvae killed by other Steinernema spp. and S. scapterisci is significant since the wax moth larvae can be used to test insects to differentiate between S. scapterisci and all other species and strains of Steinernema known currently.

Preliminary work with isoelectric focusing electrophoresis showed that the protein patterns of S. scapterisci were different from those of Mexican and Breton strains of S. carpocapsae.

Steinernema scapterisci n. sp. can be distinguished from other species of steinernema as follows: S. glaseri by the presence of a mucron on the tail of the male of S. scapterisci, and by the shorter third stage infective juvenile of S. scapterisci (517–609 µm) compared to that of S. glaseri (860–1500 µm); from S. bibionis and S. intermedia by the shorter third stage juvenile (700–1000 µm for S. bibionis and 608–800 µm for S. intermedia); from S. carpocapsae by the ratio of head to excretory pore divided by tail length, this ratio is 0.73 (0.60–0.80) in S. scapterisci compared to 0.60 (0.54–0.66) in S. carpocapsae [Poinar, Recognition of Neoaplectana species (Steinernematidae: Rhabditida). Proc. Helminthol. Soc. Wash., Vol. 53, pages 121–129 (1986)]; and by the shape of the tail of the third stage juvenile; when relaxed, the tail of S. scapterisci usually curves ventrally forming an angle about 110° with the body. The ratio of head to excretory pore/head to end of esophagus is 0.31 compared to 0.65 in S. glaseri, 0.45 in S. bibionis, 0.51 in S. intermedia and 0.26 in S. carpocapsae.

S. scapterisci n. sp. also can be separated from all other species by the following characteristics: The first generation female has large cheilorhabdions (about 4.8 µm thick by 5.8 µm long in lateral view of normal-sized female), an elliptically-shaped structure in the excretory canal, and a prominent double-flapped epiptygma. Males of both generations have brown spicules which are pointed and taper smoothly to the end; distal end of the blade is narrow; shaft long and bearing a sheath; gubernaculum with long and upward-bent anterior part.

S. scapterisci n. sp. cannot be cultured on wax moth larvae (Galleria mellonella), but sometimes a few wax moth larvae will be killed by the nematode. When this occurs, the bodies of the wax moth larvae turn black, while those killed by other species of Steinernema turn whitish or yellowish, but never black. Other species of Steinernema develop very well in wax moth larvae. Finally, this nematode can be distinguished from other species by bioassay on 3 insects: fall army worm, velvet bean caterpillar and wax moth larvae. In two days, other species of Steinernema will kill 100% of the test insects, but *S. scapterisci* will kill no more than about 10% thereof (Table 4).

TABLE 3

Measurements (in μm) of the Third Stage Juveniles of *Steinernema scapterisci* n. sp. (n = 20)

| Character | Mean | SD | Range |
|---|---|---|---|
| Body length | 572 | 27 | 517–609 |
| Greatest width | 24 | 4 | 18–30 |
| EP | 39 | 4 | 36–48 |

TABLE 1

Measurements (in μm) of First and Second Generation Females of *Steinernema scarterisci* n. sp. (n = 10)

| Character | First Generation | | | Second Generation | | |
|---|---|---|---|---|---|---|
| | Mean | (SD) | Range | Mean | (SD) | Range |
| Body length | 4162 | (540) | 3531–5156 | 2209 | (223) | 1841–2530 |
| Greatest width | 179 | (13) | 159–203 | 123 | (14) | 94–141 |
| Stoma length | 7.5 | (1) | 6–9 | 6.7 | (1.4) | 5–9 |
| Stoma width | 10 | (3) | 9–12 | 8.9 | (0.9) | 8–11 |
| EP | 89 | (5) | 78–94 | 78 | (6.8) | 66–88 |
| NR | 174 | (13) | 153–194 | 169 | (12) | 147–184 |
| ES | 242 | (17) | 219–269 | 241 | (15) | 222–266 |
| Tail length | 46 | (8) | 34–59 | 58 | (4) | 48–64 |
| Anal body width | 58 | (9) | 41–72 | 47 | (2.8) | 43–52 |
| Percentage vulva | 53 | (2) | 50–54 | 52 | (2) | 52–60 |
| EP:ES | 0.37 | (0.03) | 0.32–0.41 | 0.32 | (0.3) | 0.28–0.36 |

EP = Distance from anterior end to excretory pore
NR = Distance from anterior end to nerve ring
ES = Distance from anterior end to end of esophagus

TABLE 2

Measurements (in μm) of First and Second Generation Males of *Steinernema scarterisci* n. sp. (n = 10)

| Character | First Generation | | | Second Generation | | |
|---|---|---|---|---|---|---|
| | Mean | (SD1) | Range | Mean | (SD) | Range |
| Body length | 1728 | (358) | 1319–2271 | 1147 | (95) | 1031–1342 |
| Greatest width | 156 | (49) | 97–231 | 73 | (8) | 62–84 |
| Stoma length | 4.4 | (1) | 3–5 | 4.3 | (1) | 3–6 |
| Stoma width | 6.1 | (1) | 5–8 | 6.0 | (1.2) | 5–8 |
| EP | 71 | (11) | 63–98 | 68 | (7) | 50–75 |
| NR | 136 | (11) | 120–152 | 121 | (10) | 103–131 |
| ES | 187 | (21) | 164–216 | 168 | (13) | 138–181 |
| Testis flexure | 374 | (52) | 306–447 | 205 | (19) | 176–234 |
| Anal body width | 33 | (5) | 31–45 | 33 | (4) | 28–41 |
| Tail length | 25 | (3) | 21–30 | 25 | (3) | 22–30 |
| Spicule length | 83 | (5) | 72–92 | 78 | (3) | 75–83 |
| Spicule width | 13 | (4) | 13–14 | 12 | (1) | 11–14 |
| Gubernaculum length | 65 | (5) | 59–75 | 54 | (3) | 47–59 |
| Gubernaculum width | 8 | (0.5) | 8–9 | 6 | (0.7) | 5–8 |
| EP:ES | 0.36 | (0.02) | 0.32–0.39 | 0.40 | (0.06) | 0.29–0.52 |
| Mucron length | 4.3 | (0.6) | 3.1–4.7 | 3.9 | (0.6) | 3.1–4.6 |

EP = Distance from anterior end to excretory pore
NR = Distance from anterior end to nerve ring
ES = Distance from anterior end to end of esophagus

TABLE 3-continued

Measurements (in μm) of the Third Stage Juveniles
of *Steinernema scapterisci* n. sp. (n = 20)

| Character | Mean | SD | Range |
| --- | --- | --- | --- |
| NR | 97 | 1.1 | 83–106 |
| ES | 127 | 6 | 113–134 |
| Tail length | 54 | 3 | 48–60 |
| EP:ES | 0.31 | 0.03 | 0.27–0.40 |
| EP:Tail length | 0.73 | 0.06 | 0.60–0.80 |

EP = Distance from anterior end to excretory pore
NR = Distance from anterior end to nerve ring
ES = Distance from anterior end to end of esophagus

TABLE 4

Percentage of Four Species of Lepidopterous
Insects Killed Within 48 Hours by Steinernema spp.

| | Percentage of insects killed + | | | |
| --- | --- | --- | --- | --- |
| Nematode | FAW | VBC | GCW | WML |
| *S. glaseri* | 100 | 90 | 50 | 100 |
| *S. bibionis* | 100 | 90 | 55 | 100 |
| *S. carpocapsae* | | | | |
| Breton | 100 | 100 | — | 100 |
| Italian | 100 | 100 | — | 100 |
| Mexican | 100 | 100 | 80 | 100 |
| Agriotos | 100 | 100 | 20 | 100 |
| All | 100 | 100 | — | 100 |
| *S. scapterisci* | 8 | 3 | 10 | 9 |
| Control | 0 | 0 | 0 | 0 |

+ = Average of four trials
FAW = fall army worm
VBC = velvet bean caterpillar
GCW = granulate cut worm
WML = wax moth larvae

EXAMPLE 1

*Steinernema scapterisci* was tested against potential host insects, except for honeybees, as follows: The test host insects were placed in petri dishes containing two filter papers. Then 8,000 to 12,000 infective third stage juveniles of *S. scapterisci* in a water suspension were placed by pipette onto the filter papers. Lids were placed on the petri dishes and the dishes maintained in the dark at room temperature. A minimum of 30 insects was used per test. The specimens were observed each 24 hours to determine the number living and dead. Experiments were terminated after 48 to 72 hours. The numbers of dead insects were converted to percentages killed using Abbott's formula which is:

$$\frac{(X-Y)}{X} \times 100 = \% \text{ kill}$$

wherein:

X = % living of untreated control insects; and

Y = % living of nematode-treated insects.

Honeybee experiments were conducted in 5 cages for the treated and 5 cages for the controls with 20 honeybees in each cage. The experiment was repeated once. Five thousand nematodes were placed on water-saturated cotton contained in a petri dish. This served as the only source of water for the honeybees. Exposure to the nematodes occurred each time they visited the water source. The experiment was checked each 24 hours for living and dead honeybees and terminated after 72 hours. Abbott's formula was used to express percentage kill. The results are set forth in Table 5.

TABLE 5

| Insects killed by S. scapterisci | |
| --- | --- |
| Host | % Kill |
| Mole crickets (*Scapteriscus* spp.) | >90 |
| Field crickets (*Gryllus rubens*) | 14 |
| Honeybees (*Apis mellifera*) | 11 |
| Granulate cut worms (*Agriotis suterranea*) | 10 |
| Wax moth larvae (*Galleria mellonella*) | 4 |

The above data show that *S. scapterisci* has a high degree of specificity to mole crickets. The data are significant, also, in that only 4% of wax moth larvae were killed, whereas wax moth larvae are used as hosts to produce all other strains of the nematode in vivo.

EXAMPLE 2

Field Tests of *S. scapterisci*

Field releases of the nematode were made in 1985 in two 7×7 meter (=49 square meters) plots to determine if the nematode could survive in the Florida environment and to obtain some information on rate of kill of mole crickets. The nematodes were applied by two different methods at a rate of 200,000 infective third stage juveniles per square meter. One method was to mix the nematodes in water and apply them from sprinkling cans onto the plots. The other method was to bury per square meter four dead mole crickets which had been infected with the nematode in the laboratory. (We obtained about 50,000 infective stage juvenile nematodes from each infected mole cricket.) The initial kill rates in these plots averaged about 30% of those mole crickets caught in pitfall traps placed in the center of each plot. The kill rates dropped off to about 10% of those mole crickets trapped over the next year. Thus, the nematode survives both summers and winters in Florida, but the plots were too small to avoid reinfestation by mole crickets from outside the plots.

Water or other aqueous media and infected, dead mole crickets have been used as means for distributing the nematodes. There is no reason that other carriers which do not cause the nematodes to die from desiccation would not be suitable An attractant for mole crickets (e g , COAX®, sucrose, maltose, malt extract or molasses) may be included in the composition.

An alternative method is to trap mole crickets, infect them with the nematode and then release them before they become too sick to be active, so that they will distribute the nematode outward from the release site and also in the soil where mole crickets bury. Another method to use during the flight season of the mole crickets is to infest a small plot of ground (5×5 meters, for example) with large numbers of nematodes, perhaps 400,000 or more per square meter, place an electronic caller (a device which mimics the song of mole crickets to which they are attracted) in the center of the area and let the mole crickets become infected when they land in the infested area. When the electronic caller is turned off, the infected mole crickets will fly from the site and thus disperse the nematode when they die. Other mole crickets will, in turn, become infected from those sites and increase the dispersion area of the nematode when those mole crickets die.

Generally, amounts of composition (nematodes plus carrier) are applied so as to provide from about 100,000 to about 200,000 nematodes per square meter of leaf or soil.

A further embodiment of the invention comprises the use of a strain of *S. scapterisci* having an enhanced insecticidal activity. The new strains are developed by passage of a first infective third stage of the nematode through the targeted insect, i.e., by infecting a targeted species of insect with infective third stage juveniles of the nematode. Some of those nematodes successfully penetrate into the hemocoel and reproduce limitedly inside the body. Some of their offspring also reproduce in the same insect cadaver and a few of their progeny exit the cadaver as infective third stage juveniles. These juveniles may optimally be inoculated into e.g., house crickets (*Acheta domestica*) to increase their numbers. The third stage juveniles that emerge from house cricket cadavers are exposed to other targeted species of insects. A greater number penetrates into the body and reproduces the second time resulting in a greater number of third stage juveniles exiting from the targeted species cadavers. If numbers are still low, however, these can be inoculated into house crickets to increase their numbers.

It is preferred to conduct a serial passage of the nematodes through the targeted insect, i.e., repeating at least once the steps of (1) infecting insects of the targeted species with nematodes, and (2) collecting infective third stage juveniles which emerge from insects killed by the repeated infection, wherein the repeated infection is effected with the infective third stage juveniles produced previously; the infective third stage juveniles produced by the repeated infection have a greater degree of insecticidal activity than those produced previously.

The steps of infection and collection of infective third stage juveniles are effected until a maximum degree of insecticidal activity in the collected third stage juveniles is achieved.

The host species of insect utilized to increase the numbers of infective third stage juveniles may comprise any insect life stage that is a suitable host of the nematode. Such third stage juvenile nematodes also may be increased in vitro by using a suitable culture medium for the bacterium on which they feed. Such a medium is disclosed in U.S. Pat. No. 4,178,366, the disclosure of which is incorporated herein by reference. Another good medium can be made from vegetable or animal oil, hog or beef liver and water applied to an inert carrier, e.g., cellulose sponge. One such formulation is 50 grams of macerated liver, 2 ml of cooking oil and 250 ml of water mixed and absorbed into 20 grams of sponge.

EXAMPLE 3

The original strain of *S. scapterisci* collected from the field killed 38% of the mole cricket species, *Scapteriscus acletus*, into which they were inoculated. The infective third stage juveniles which emerged from the dead mole crickets were inoculated into other mole crickets, both *S. acletus* and *S. vicinus*. Progeny from these nematodes have been used in all other tests.

EXAMPLE 4

Experiments were conducted in 3- or 5-gallon size buckets of soil to compare different methods of adding infective stage *S. scapterisci* to the soil and the period of time over which kill of mole crickets would occur without adding more nematodes.

Treatments were: 1 infected mole cricket, 2 infected mole crickets, 12,000 nematodes sprayed on the soil surface and untreated control. It was calculated that about 50,000 nematodes would emerge from each mole cricket carcass, but would not move far from the carcass. The spray application was equivalent to 180,000 nematodes per square meter.

Ten mole crickets (uninfected) were released into each bucket. Ten days later, the number of dead and living mole crickets was determined and the percentage kill calculated based on Abbott's formula. Again, ten uninfected mole crickets were released in the buckets and the process was repeated for a total of four releases. The results are set forth in Table 6.

TABLE 6

| Adjusted % kill of *Scapteriscus vicinus* | | | | |
|---|---|---|---|---|
| | Release | | | |
| Inoculum | 1 | 2 | 3 | 4 |
| 1 infected mole cricket | 29 | 43 | 18 | 10 |
| 2 infected mole crickets | 38 | 47 | 12 | 12 |
| 12,000 nematodes | 34 | 70 | 27 | 9 |
| **Adjusted % kill of *Scapteriscus acletus*** | | | | |
| | Release | | | |
| Inoculum | 1 | 2 | 3 | 4 |
| 1 infected mole cricket | 12 | 26 | 12 | 17 |
| 2 infected mole crickets | 3 | 22 | 4 | 0 |
| 12,000 nematodes | 19 | 48 | 12 | 0 |

The methods, compositions and products of the present invention are highly advantageous in that the nematodes employed, unlike those currently in use, do reproduce in the target insect species and, hence, recycle in nature to continue controlling the insect over long periods of time.

In plot tests (50 square meters) conducted over a span of years, the population of, for example, mole crickets has declined about 95% after a single application of the nematodes and has remained at that level for five years after application. Moreover, in these tests, the nematode has been recovered some ten miles from the nearest release site.

The methods, compositions and products of the invention are also advantageous in controlling other pests of the order Orthoptera such as, e.g., the house cricket (*Acheta domestica*), the southeastern field cricket (*Gryllus rubens*), the field crickets (*Gryllus spp.*), the American cockroach (*Periplaneta americana*), the Eastern lubber grasshopper (*Romalea guttata*), locusts, the Mormon cricket, etc.

EXAMPLE 5

A partial host range was determined by testing American cockroach (*Periplaneta americana*), fall army worm (*Spodoptera frugiperda*), field cricket (*Gryllus spp.*), granulate cut worm (*Feltia subterranea*), honeybee (*Apis mellifera*), house cricket (*Acheta domestica*), wax moth larva (*Galleria mellonella*), velvet bean caterpillar (*Anticarsia gemmatalis*) and two beetle predators of mole crickets, *Megacephala virginica* and *Pasimachus sublaevis*.

The tests were conducted in 100×15 mm petri dishes except for the honeybees. Two pieces of Whatman No. 2 filter paper were placed in a petri dish and 5,000 to 8,000 infective juveniles in 2 ml of water were added. Five to ten insects, previously anesthetized by $CO_2$, were placed in each dish and the dishes were stored in the dark. Controls contained the insects, but no nematodes. Treatments were replicated five to ten times. The number of dead insects was determined after three days.

Only ten of each of the mole cricket predators were available. These were placed in a 150×25 mm petri dish prepared as above. After three days, the dead predatory insects were dissected to see if the nematodes were developed within the body. The results are set forth in Table 7.

TABLE 7

Percentage of Different Insects Killed By *Steinernema scapterisci*

| Insect | % Kill* |
| --- | --- |
| Mole cricket (*Scapteriscus* spp.) | 100 |
| House cricket (*Acheta domestica*) | 100 |
| Field cricket (*Gryllus* spp.) | 22 |
| Granulate cut worm (*Feltia subterranea*) | 10 |
| Wax moth larva (*Galleria mellonella*) | 9 |
| Fall army worm (*Spodoptera frugiperda*) | 8 |
| Cockroach (*Periplaneta americana*) | 4 |
| Honeybee (*Apis mellifera*) | 3 |
| Velvet bean caterpillar (*Anticarsia gemmatalis*) | 3 |
| Predatory beetle (*Megacephala virginica*) | 0 |
| Predatory beetle (*Pasimachus sublaevis*) | 0 |

*The percentages in the table are corrected using Abbott's formula.

The compositions and products of the invention are shown by the results set forth in Table 7 to be effective against house crickets, field crickets and cockroaches, as well as mole crickets. As will be understood by those skilled in the art, optimization of application parameters will yield higher kill figures for the desired targeted pest species.

EXAMPLE 6

The tests of Example 5 were repeated with other pest species of the order Orthoptera (except that the tests were conducted in vials rather than in petri dishes) as follows:

The type of arena, substratum and inoculum were similar to the experiments with *Scapteriscus spp*. The treatments were 0, 10, 100, 1,000, 5,000 and 10,000 nematodes per replication delivered in 1.0 ml deionized water. The experimental design was a randomized complete block with five replications of five insects each. Incubation conditions, mortality assessment and data analysis were the same as in the previous experiments.

Pathogenicity to *Romalea guttata*

Two experiments were conducted with this insect. The arenas consisted of 5.4 cm×2.7 cm plastic vials with filter paper lining the inner surface, except for a longitudinal hiatus of approximately 0.5 cm. After the nematodes and one insect were introduced into each vial, the top was covered with two layers of cheesecloth held in place with a rubber band. Vials were maintained at 25° C. inside plastic bags which were open at the top.

Experiment 1

Treatments were 0, 100, 1,000 and 10,0000 nematodes per replication, delivered in 0.5 ml of deionized water. The experimental design was a randomized complete block with six replications of five insects each. Mortality was determined at 24, 48, 72 and 96 hours.

Mortality greater than that of the control was obtained with 10,000 nematodes at 24 hours (Table 8). Mortality above 50% was obtained with treatments of 1,000 and 10,000 nematodes at 48, 72 and 96 hours after exposure (Table 8).

TABLE 8

Percent Mortality of *Romalea guttata* From *Steinernema scanterisci* in Laboratory Tests (Experiment 1)

| Inoculum level | Time After Inoculation (hours) | | | |
| --- | --- | --- | --- | --- |
| | 24 | 48 | 72 | 96 |
| 0 | — a | — a | 10.0 a | 16.7 a |
| 100 | — a | 33.3 b | 50.0 b | 53.3 b |
| 1,000 | — a | 66.7 c | 80.0 c | 80.0 c |
| 10,000 | 33.3 b | 100.0 d | 100.0 c | 100.0 c |

*Data are percent mortality from six replications composed of five insects each.
Means in columns followed by the same letter are not significantly different ($P = 0.05$).

Experiment 2

Methods were identical to those for Experiment 1 with this insect species, except that treatments were 0, 100 and 1,000 nematodes per vial.

With inoculum levels of 100 and 1,000 nematodes, mortality levels in this experiment were generally similar to those observed in Experiment 1 (Table 9). However, mortality levels of 50% or greater were achieved 24 hours earlier in Experiment 1 than in Experiment 2 for the 100 and 1,000 nematode inoculum levels (Table 9).

TABLE 9

Percent Mortality of *Romalea guttata* From *Steinernema scapterisci* in Laboratory Tests (Experiment 2)

| Inoculum level | Time After Inoculation (hours) | | | |
| --- | --- | --- | --- | --- |
| | 24 | 48 | 72 | 96 |
| 0 | — a | 10.0 a | 15.0 a | 15.0 a |
| 100 | — a | 35.0 a | 40.0 ab | 50.0 b |
| 1,000 | — a | 30.0 a | 65.0 b | 70.0 b |

*Data are percent mortality from four replications composed of five insects each.
Means in columns followed by the same letter are not significantly different ($P = 0.05$).

Pathogenicity to *Gryllus rubens*

Significant differences in mortality from the 0 dose control were obtained with doses of 1,000 nematodes at 24 hours (Table 10). Only 10,000 nematodes induced mortality of taking into account the mortality in the control. At 48 and 72 hours, all the nematode doses gave mortality significantly higher than the control (Table 10).

TABLE 10

Percent Mortality of *Gryllus rubens* From *Steinernema scapterisci* in Laboratory Tests*

| Inoculum level | Time After Inoculation (hours) | | | |
| --- | --- | --- | --- | --- |
| | 24 | 48 | 72 | 96 |
| 0 | 9.0 a | 22.0 a | 32.0 a | 64.0 a |
| 10 | 20.0 ab | 56.0 b | 48.0 b | 76.0 ab |
| 100 | 24.0 abc | 58.0 b | 76.0 c | 88.0 bc |

TABLE 10-continued

Percent Mortality of *Gryllus rubens* From
*Steinernema scapterisci* in Laboratory Tests*

| Inoculum level | Time After Inoculation (hours) | | | |
|---|---|---|---|---|
| | 24 | 48 | 72 | 96 |
| 1,000 | 40.0 bcd | 75.0 bc | 84.0 c | 96.0 c |
| 5,000 | 52.0 cd | 96.0 c | 100.0 d | 96.0 c |
| 10,000 | 64.0 c | 92.0 c | 100.0 d | 100.0 c |

*Data are percent mortality from five replications composed of five insects each.
Means in columns followed by the same letter are not significantly different (P = 0.05).

The letters (a,b,c,d) in the columns of the tables hereinabove indicate whether statistical differences exist. For example, in the last column of Table 10, the mortality rate for 0 and 10 inoculum levels are different from those of 1,000, 5,000 and 10,000 inoculum levels.

The results demonstrate the pathogenicity of the compositions and products of the present invention to a wide variety of species of the order Orthoptera.

EXAMPLE 7

In order to determine whether *Steinernema scapterisci*, which had been developed specifically to kill mole crickets, would kill German cockroaches, *Blatella germanica*, or could be modified if necessary to do so, a series of experiments were conducted. In each of the experiments, 10,000 infective stage juveniles of *S. scapterisci* in 2 ml of water were placed on filter paper in petri dishes and 10 German cockroaches were added. The dishes were stored in the dark at room temperature. After four days, the number of dead cockroaches was determined. In Experiment 1, each treatment was replicated five times and, in all other experiments, each treatment was replicated ten times. Abbott's formula was used to correct for percent kill of cockroaches.

Experiment 1

52% of the cockroaches exposed to the nematodes were killed (Table 11, first passage). The infective juveniles that emerged from the cockroach cadavers were collected and used in Experiment 2.

Experiment 2

73.7% of the cockroaches exposed to the nematodes were killed (Table 11, second passage).

In order to increase the population of the nematodes for additional experiments, the infectire juveniles which emerged from the cockroach cadavers were passed twice through house crickets and once through mole crickets. These infecrive juveniles were used in Experiment 3.

Experiment 3

This experiment was repeated twice. In one repetition, 97.9% of the cockroaches were killed by the nematodes and, in the other repetition, 82.8% were killed (Table 11, third passage) for an average of 90.3% kill.

To determine if the 90% kill rate of cockroaches would persist if the nematodes were passed back through house crickets and mole crickets, infectire juveniles were collected from Experiment 3 and passed through house crickets and mole crickets. Infectire juveniles collected from house crickets were used in Experiment 4, while those from mole crickets were used in Experiment 5.

TABLE 11

Percentage Kill of German Cockroach (*Blatella germanica*)
After Exposure for Four Days to 10,000 Infective Juveniles
of *Steinernema scarterisci*

| | Percent Kill per Replicate | | | | | | | |
|---|---|---|---|---|---|---|---|---|
| | 1st passage | | 2nd passage | | 3rd passage | | | |
| | | | | | Repetition 1 | | Repetition 2 | |
| Rep | TRMT | CONT | TRMT | CONT | TRMT | CONT | TRMT | CONT |
| 1 | 5 | 0 | 5 | 0 | 10 | 0 | 7 | 0 |
| 2 | 7 | 0 | 7 | 0 | 10 | 1 | 7 | 0 |
| 3 | 4 | 0 | 8 | 1 | 9 | 0 | 8 | 1 |
| 4 | 5 | 0 | 7 | 0 | 10 | 0 | 8 | 0 |
| 5 | 5 | 0 | 7 | 0 | 10 | 0 | 6 | 0 |
| 6 | — | — | 7 | 0 | 10 | 0 | 7 | 0 |
| 7 | — | — | 8 | 0 | 10 | 1 | 9 | 0 |
| 8 | — | — | 8 | 0 | 9 | 1 | 8 | 0 |
| 9 | — | — | 9 | 0 | 10 | 0 | 8 | 0 |
| 10 | — | — | 6 | 1 | 10 | 0 | 8 | 0 |
| TOTAL | 52 | 0 | 74 | 2 | 98 | 3 | 83 | 1 |
| % KILL+ | 52 | | 73.7 | | 97.9 | | 82.8 | |

+Corrected by Abbott's formula
Rep = Replicate
TRMT = Treatment
CONT = Control (untreated)

Experiment 4

After being passed back through house crickets, the nematodes killed 68% of the cockroaches (Table 12).

TABLE 12

Percentage Kill of German Cockroach (*Blatella germanica*)
By *Steinernema scapterisci* After Three Passages
Through German Cockroach and One passage
Through House Cricket

| Replicate | Treatment | Control |
|---|---|---|
| 1 | 4 | 0 |
| 2 | 7 | 0 |
| 3 | 2 | 1 |
| 4 | 5 | 0 |
| 5 | 5 | 0 |
| 6 | 10 | 0 |
| 7 | 10 | 1 |
| 8 | 10 | 0 |
| 9 | 7 | 0 |
| 10 | 9 | 1 |
| TOTAL | 69 | 3 |
| % KILL[+] | 68 | |

[+]Corrected by Abbott's formula

Experiment 5

After being passed back through mole crickets, the nematodes killed 69.4% of the cockroaches (Table 13).

TABLE 13

Percentage Kill of German Cockroach (*Blatella germanica*)
By *Steinernema scapterisci* After Three Passages
Through German Cockroach and One passage
Through Mole Cricket

| Replicate | Treatment | Control |
|---|---|---|
| 1 | 8 | 1 |
| 2 | 9 | 0 |
| 3 | 6 | 1 |
| 4 | 4 | 0 |
| 5 | 7 | 0 |
| 6 | 7 | 0 |
| 7 | 8 | 1 |
| 8 | 7 | 0 |
| 9 | 8 | 1 |
| 10 | 6 | 0 |
| TOTAL | 70 | 2 |
| *KILL[+] | 69.4 | |

[+]Corrected by Abbott's formula

These experiments show that it is possible to increase the percentage kill of cockroaches by *S. scapterisci* by selecting the infective juveniles which emerge from cadavers in which the nematode reproduces and passing those juveniles through other cockroaches. As indicated in Experiment 3, by passing *S. scapterisci* repeatedly through the German cockroach, one can obtain a strain that will consistently kill 90% or more of the population.

From the experimental data presented herein, it should be apparent to those skilled in the art that the kill rate of *S. scapterisci* to other untested insects in the order Orthoptera, such as the American cockroach, would be enhanced just as has been done for mole crickets and German cockroaches.

We claim:

1. A method of biologically controlling pest insects in the order Orthoptera selected from the group consisting of grasshoppers, cockroaches, field crickets and house crickets comprising contacting so as to infect said insects with an insecticidal amount of infective third stage of *Steinernema scapterisci* nematodes having ATCC Deposit No. 75197.

2. The method of claim 1 wherein said infective third stage of *Steinernema scapterisci* nematodes is produced by passage of a first infective third stage of said nematodes through said insects to produce a second infective third stage of said nematodes having a greater degree of insecticidal activity than said first infective third stage.

* * * * *